US00PP10451P

United States Patent [19]

Shaw

[11] Patent Number: Plant 10,451

[45] Date of Patent: Jun. 16, 1998

[54] STRAWBERRY PLANT NAMED 'AROMAS'

[75] Inventor: Douglas V. Shaw, Davis, Calif.

[73] Assignee: The Regents of the University of California, Oakland, Calif.

[21] Appl. No.: 747,506

[22] Filed: Nov. 12, 1996

[51] Int. Cl.[6] ..... A01H 5/00

[52] U.S. Cl. ..... Plt./49

[58] Field of Search ..... Plt./48, 49

*Primary Examiner*—James R. Feyrer

*Attorney, Agent, or Firm*—Burns, Doane, Swecker & Mathis, L.L.P.

[57] ABSTRACT

'CN209' is a new and distinct cultivar of strawberry plant of the day-neutral type which has larger fruit and produces greater yields than 'Selva' or 'Seascape' when treated with appropriate planting regimes. Production for 'CN209' initiates slightly later than for the comparison cultivars and it produces substantially larger quantities of late-season fruit.

3 Drawing Sheets

RELATED APPLICATIONS

There are no related applications.

FIELD OF THE INVENTION

This invention relates to a new and distinctive day-neutral type cultivar designated as 'CN209' also known as 'Aromas', which resulted from a cross performed in 1991 between advanced selections Cal 87.112-6 and Cal 88.270-1. This cultivar is botanically identified as *F.×ananassa Duch.*

'CN209' was first fruited at the University of California Wolfskill Experimental Orchard, near Winters, Calif. in 1992, where it was selected, originally designated Cal 91.248-3, and propagated asexually by runners. Following selection and during testing the plant of this disclosure was designated 'CN209'. With the decision that this plant was to be released, it was given the name 'Aromas' for the purposes of introduction into commerce and for international registration and recognition. Asexual propagules from this original source have been tested at the Watsonville Strawberry Research Facility, the South Coast Research and Extension Center, and to a limited extent in grower fields starting in 1994.

DETAILED DESCRIPTION OF THE INVENTION

Figure 1:
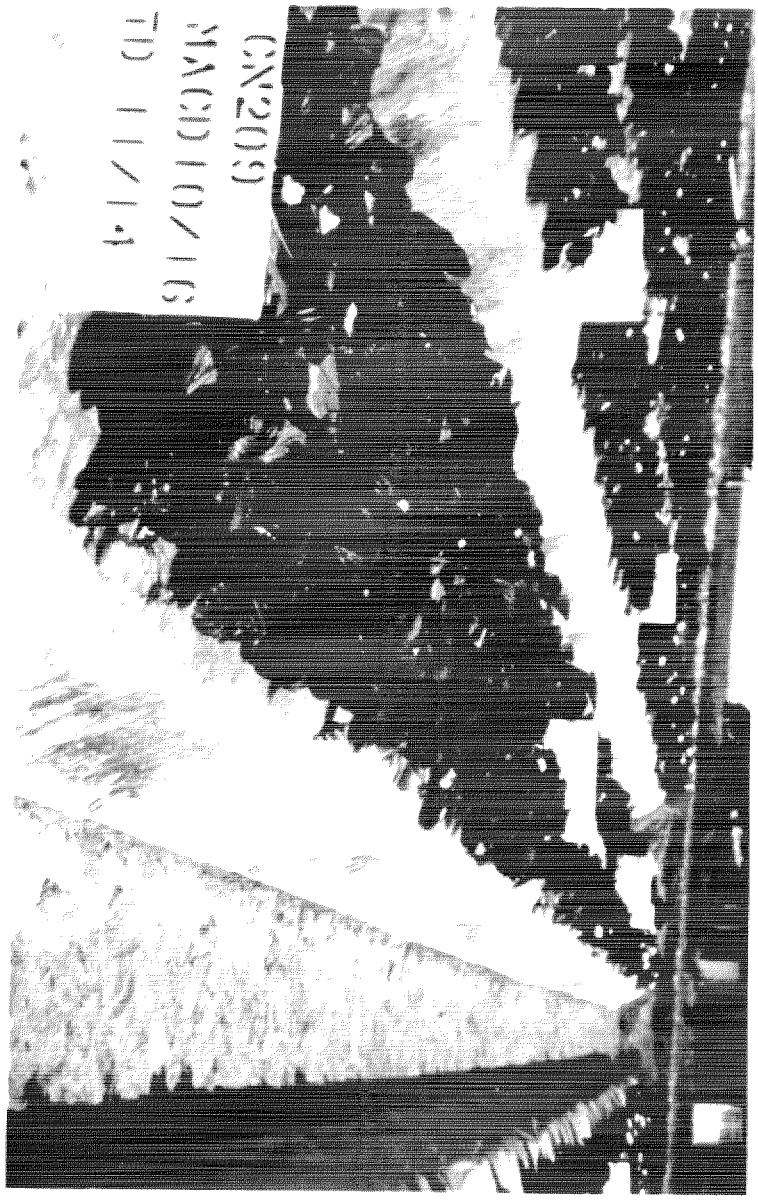
FIG. 1 depicts the general flowering and fruiting characteristics of the plant.
Figure 2:
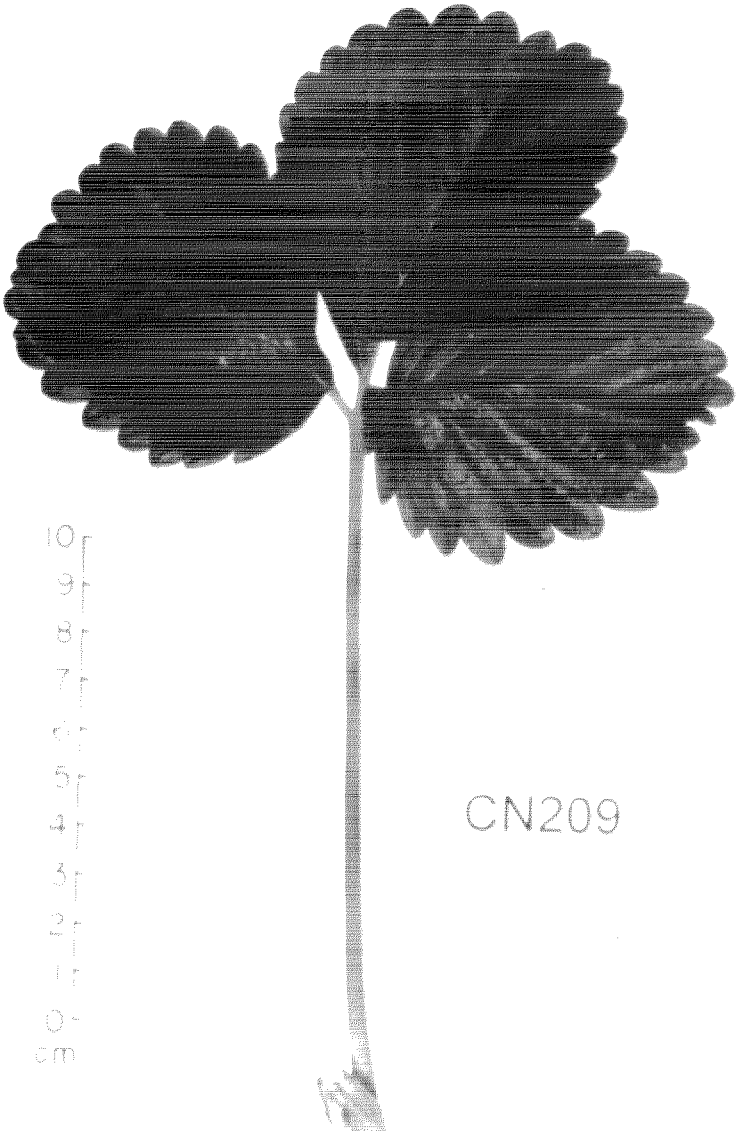
FIG. 2 depicts a typical mature leaf during late spring.
Figure 3:
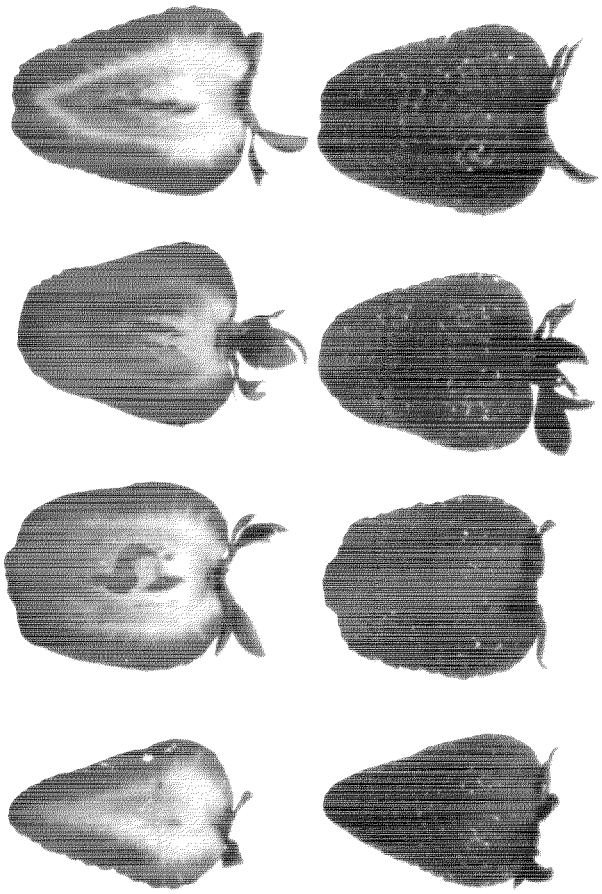
FIG. 3 depicts representative mid-season fruit.

'CN209' is moderate to weak in expressing the day-neutral character, being a stronger day-neutral than 'Seascape' (U.S. Plant Pat. No. 7,614), comparable or slightly more day-neutral than 'Selva' (U.S. Plant Pat. No. 5,266), and less so than 'Fern' (U.S. Plant Pat. No. 5,267) or 'Irvine' (U.S. Plant Pat. No. 7,172). The production pattern for 'CN209' is similar to that for 'Selva' or 'Seascape', and it will be of special interest for winter plantings, where 'Selva' and 'Seascape' have been successful and summer plantings where 'Seascape' has been successful.

Plants and Foliage

Fruiting plants of 'CN209' are more erect and usually more vigorous than plants of 'Selva' or 'Seascape'. With appropriate treatment, 'CN209' is a slightly larger plant than 'Selva', and similar in size to 'Seascape'. Comparative statistics for foliar characters near mid-season are given for the three cultivars in Table 1. Leaflets are somewhat smaller and more rounded than leaves of 'Selva' or 'Seascape'. Leaves including petioles are somewhat longer and more narrow than the comparison cultivars. Petioles are thicker and more stiff than those of 'Selva' and are similar to those of 'Seascape'. 'CN209' has variable leaf convexity, generally more concave than leaves of 'Selva', and has fewer and more rounded serrations than the comparison cultivars. The adaxial (upper) leaf surface for 'CN209' is darker and more glossy than for the comparison cultivars, whereas the abaxial surface is slightly lighter (Table 2)

Isozymes in Leaf Extracts

'CN209' has been classified for three isozyme systems using starch gel electrophoresis (Table 3): Phosophoglucoisomerase (PGI), Leucine Aminopeptidase (LAP), and Phosphoglucomutase (PGM). It is distinguishable from 'Selva' but not from 'Seascape' using this methodology. For electrophoretic procedures see: J. Amer. Soc. Hort. Sci. 106:684–687.

Disease and Pest Reaction

'CN209' is moderately susceptible to common leaf spot (*Ramularia tulasnei*) and Verticillium wilt (*Verticillium dahliae*), relatively resistant to powdery mildew (*Sphaerotheca macularis*) and Anthracnose crown rot (*Colletotrichum acutatum*). When treated properly, it has tolerance to two-spotted spidermites (*Tetranychus urticae*) greater than 'Seascape' and 'Selva'. 'CN209' is tolerant to strawberry viruses encountered in California.

TABLE 1

Foliar characteristics for 'CN209', 'Selva', and 'Seascape'.

| Foliar Character | Cultivar | | |
|---|---|---|---|
| | 'Selva' | 'Seascape' | 'CN209' |
| | Mid-tier leaflet | | |
| Length (mm) | | | |
| mean | 72.6 | 72.8 | 66.3 |
| range | 65–88 | 65–82 | 60–77 |

TABLE 1-continued

Foliar characteristics for 'CN209', 'Selva', and 'Seascape'.

| Foliar Character | Cultivar 'Selva' | 'Seascape' | 'CN209' |
|---|---|---|---|
| Width (mm) | | | |
| mean | 68.2 | 64.5 | 62.8 |
| range | 51–84 | 48–78 | 57–70 |
| | Mid-tier leaf | | |
| Length (mm) | | | |
| mean | 119.2 | 123.8 | 125.8 |
| range | 94–139 | 80–155 | 110–143 |
| Width (mm) | | | |
| mean | 130.1 | 127.1 | 120.5 |
| range | 111–170 | 108–150 | 105–134 |
| # leaflets/leaf | 3 | 3, rarely 4 | 3 |
| Leaf convexity | mostly flat to convex | concave to convex, mostly flat to convex | mostly flat to convex |
| | Serrations | | |
| number | few–moderate | moderate | moderate |
| shape | round to semipointed | semiround to semipointed | semipointed |
| Leaf pubescence | moderate | moderate | moderate to heavy |
| | Petiole pubescence | | |
| density | heavy | mod. to heavy | heavy |
| direction | perpendicular | perp to slight acropetal | perpendicular |

Flowering, Fruiting, Fruit, and Production Characteristics

'CN209' is similar to other California day-neutral cultivars (e. g. 'Selva' and 'Seascape') in that it will flower independently of day length, given appropriate temperature and fertility conditions. Comparative statistics for flower and fruit characters near mid-season are given for the three cultivars in Table 4. The primary flowers for 'CN209' are similar in size, perhaps slightly larger than 'Selva' and 'Seascape'; the sepals are somewhat larger than for 'Seascape' and substantially larger than for 'Selva'. The calyx for 'CN209' varies from slightly indented to even, and each primary flower has 5–6 petals. The fruit shape for 'CN209' can vary but is typically a short conic, sometimes heart-shaped or slightly flattened, and is easily distinguished from other California day-neutral cultivars. External and internal fruit color for 'CN209' are darker than for 'Selva' and slightly darker than 'Seascape', and fruit is substantially more glossy than either comparison cultivar (Table 2). Achenes vary but are red to dark red, and are slightly indented.

'CN209' has been tested under a variety of cultural regimes, and optimal performance is obtained when nursery treatments and nutritional programs similar to those for 'Selva' and 'Seascape' are used. In general, 'CN209' is more vigorous than the comparison cultivars but requires similar chilling to insure fruit quality. 'CN209' retains good fruit quality in summer planting systems, similar to 'Seascape'.

When treated with appropriate planting regimes, 'CN209' has larger fruit and produces greater yields than 'Selva' or 'Seascape' (Table 5). Production for 'CN209' initiates slightly later than for the comparison cultivars and it produces substantially larger quantities of late-season fruit. Commercial appearance ratings have been superior to those for the comparison cultivars. Fruit firmness is similar to that for 'Selva' and greater than that for 'Seascape'. Subjectively, 'CN209' has very good flavor, substantially better than 'Selva', and equal to that for 'Seascape'. The fruit will be outstanding for both fresh market and processing, and will be useful for home garden purposes.

TABLE 2

Foliar and fruit color characteristics for 'CN209', 'Selva', and 'Seascape'

| Color Character | Cultivar 'Selva' | 'Seascape' | 'CN209' |
|---|---|---|---|
| | Leaf color (CIELAB) | | |
| Adaxial | | | |
| L* | | | |
| mean | 31.9 | 29.1 | 30.3 |
| range | 30.2–33.7 | 26.9–32.3 | 29.6–30.8 |
| a* | | | |
| mean | −6.5 | −5.1 | −6.2 |
| range | −5.8—7.2 | −2.4—6.6 | −5.5—6.6 |
| b* | | | |
| mean | 12.7 | 11.3 | 11.3 |
| range | 9.8–15.8 | 9.5–16.5 | 10.2–11.9 |
| Munsell | 2.5G 3/3 | 2.5GY 4/3 | 5GY 4/3 |
| Abaxial | | | |
| L* | | | |
| mean | 48.3 | 48.3 | 49.6 |
| range | 47.2–50.4 | 47.0–49.6 | 47.7–50.7 |
| a* | | | |
| mean | −7.7 | −7.2 | −7.1 |
| range | −7.3—8.3 | −6.3—8.0 | −6.5—7.6 |
| b* | | | |
| mean | 17.9 | 18.1 | 17.6 |
| range | 16.7–19.4 | 16.7–19.0 | 16.2–18.7 |
| Munsell | 7.5GY 4/4 | 10GY 4/5 | 10Y 4/3 |
| | Fruit color (CIELAB) | | |
| External | | | |
| L* | | | |
| mean | 28.5 | 25.4 | 23.3 |
| range | 23.7–33.1 | 22.7–31.5 | 20.8–24.6 |
| a* | | | |
| mean | 29.7 | 28.7 | 25.5 |
| range | 26.9–31.5 | 25.4–33.1 | 21.4–29.1 |
| b* | | | |
| mean | 16.9 | 13.7 | 10.7 |
| range | 14.4–22.1 | 9.3–19.8 | 8.7–12.5 |
| Munsell | 5R 4/12 | 5R 3/7<br>5R 4/12 | 10RP 3/10 |
| | Internal | | |
| L* | | | |
| mean | 48.8 | 45.5 | 52.4 |
| range | 44.4–53.1 | 38.3–55.0 | 48.0–57.7 |
| a* | | | |
| mean | 35.2 | 37.8 | 33.7 |

TABLE 2-continued

Foliar and fruit color characteristics for 'CN209', 'Selva', and 'Seascape'

| Color | Cultivar | | |
|---|---|---|---|
| Character | 'Selva' | 'Seascape' | 'CN209' |
| range | 31.5–39.5 | 30.8–42.7 | 24.6–37.2 |
| b* | | | |
| mean | 29.4 | 26.9 | 23.9 |
| range | 26.9–33.9 | 21.9–34.2 | 20.3–27.3 |
| Munsell | 5R 5/13 | 7R 5/13 | 5R 6/11<br>5R 5/13 |

*CIELAB is the abbreviation of the international color system known as "Commission Internationale De L'Eclairage" 1978. Recommendation on uniform color spaces - color difference equations, psychometric color terms, Supplement No. 2 to CIE Publication No. 15. PARIS.

TABLE 3

Isozyme phenotypes for 'CN209', 'Selva', and 'Seascape'.

| | Cultivar | | |
|---|---|---|---|
| locus | 'Selva' | 'Seascape' | 'CN209' |
| PGI | A2 | A4 | A4 |
| LAP | B3 | B3 | B3 |
| PGM | C2 | C2 | C2 |

TABLE 4

Flower and fruit characters for 'CN209', 'Selva', and 'Seascape'

| | Cultivar | | |
|---|---|---|---|
| Character | 'Selva' | 'Seascape' | 'CN209' |
| | # petals | | |
| mean | 5.8 | 6.1 | 5.3 |
| range | 5–8 | 5–7 | 5–6 |
| Flower position (relative to foliage) | even or interior | most even some interior or exposed | mostly even |
| Calyx diam. (mm) | | | |
| mean | 29.0 | 35.7 | 37.1 |
| range | 22–35 | 30–40 | 35–40 |
| Corolla diam. (mm) | | | |
| mean | 37.5 | 35.7 | 38.9 |
| range | 31–43 | 32–40 | 36–41 |

TABLE 4-continued

Flower and fruit characters for 'CN209', 'Selva', and 'Seascape'

| | Cultivar | | |
|---|---|---|---|
| Character | 'Selva' | 'Seascape' | 'CN209' |
| | Fruit shape | | |
| length/width | | | |
| ratio | 1.16 | 1.15 | 1.19 |
| range | 1.02–1.25 | 1.00–1.31 | 1.07–1.33 |
| subjective | conic to flat conic | mostly sharp conic | mostly rounded conic |
| Calyx position | even with shoulder | even/slight neck | slight indent |
| Seed position | even/slight extrude | slight indent to slight extrude | slight indent |

TABLE 5

Performance of 'CN209', 'Selva', and 'Seascape' evaluated at the Watsonville Research Facility in 1995 and 1996

All plants for these trials were harvested from Macdoel on Oct. 16 or 17, and planted with four weeks supplemental storage prior to planting. Harvest was initiated in early April and continued through the first week of Octover. (52" 2-row beds, 17,300 plants/acre, 100 grams/plant=316.3 crates/acre)

| Item | Yield (g/plant) | Late Yield (g/plant) | Appearance Score | Size (g/fruit) | Firmness |
|---|---|---|---|---|---|
| 'Selva' | 1,764 | 389 | 3.2 | 24.4 | 7.3 |
| 'Seascape' | 1,832 | 375 | 3.3 | 24.0 | 6.9 |
| 'CN209' | 2,094 | 452 | 3.6 | 25.4 | 7.5 |

Late yield includes harvest from August 20 through October 10.

When 'Aromas' is compared to 'Diamante' (U.S. Plant patent application Ser. No. 8/747,406, filed Nov. 12, 1996), it is found that 'Aromas' forms smaller fruit that is darker in coloration especially on interior fruit, and tends to be more productive.

We claim:

1. The new and distinct cultivar of strawberry plant substantially as herein described and illustrated.

* * * * *

CN209